United States Patent
Bauer et al.

(10) Patent No.: US 11,491,463 B2
(45) Date of Patent: Nov. 8, 2022

(54) SUPERABSORBER MIXTURES

(71) Applicant: BASF SE, Ludwigshafen (DE)

(72) Inventors: Stephan Bauer, Ludwigshafen (DE); Katrin Baumann, Ludwigshafen (DE); Markus Toennessen, Ludwigshafen (DE); Christophe Bauduin, Ludwigshafen (DE); Markus Christian Biel, Juelich (DE); Thomas Daniel, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 310 days.

(21) Appl. No.: 16/958,793

(22) PCT Filed: Jan. 2, 2019

(86) PCT No.: PCT/EP2019/050010
§ 371 (c)(1),
(2) Date: Jun. 29, 2020

(87) PCT Pub. No.: WO2019/137833
PCT Pub. Date: Jul. 18, 2019

(65) Prior Publication Data
US 2021/0362126 A1    Nov. 25, 2021

(30) Foreign Application Priority Data

Jan. 9, 2018    (EP) .................... 18150837

(51) Int. Cl.
  *B01J 20/28*    (2006.01)
  *A61L 15/60*    (2006.01)
(52) U.S. Cl.
  CPC ......... *B01J 20/28011* (2013.01); *A61L 15/60* (2013.01); *B01J 20/28019* (2013.01); *B01J 2220/68* (2013.01)

(58) Field of Classification Search
  CPC .................... B01J 20/28; B01J 20/28011; B01J 20/28019; B01J 2220/68; A61L 15/60
  USPC .......................................... 502/402
  See application file for complete search history.

(56) References Cited

U.S. PATENT DOCUMENTS

2005/0245393 A1    11/2005    Herfert et al.

FOREIGN PATENT DOCUMENTS

| DE | 60304216 T2 | 8/2006 |
|---|---|---|
| EP | 2535027 A1 | 12/2012 |
| WO | WO-2013/078109 A1 | 5/2013 |
| WO | WO-2014/79694 A1 | 5/2014 |
| WO | WO-2014/118024 A1 | 8/2014 |
| WO | WO-2016/134905 A1 | 9/2016 |
| WO | WO-2017/207330 A1 | 12/2017 |

OTHER PUBLICATIONS

International Application No. PCT/EP2019/050010, International Search Report, dated Apr. 12, 2019.
Graham, et al., "Chapter 3—Commercial Processes for the Manufacture of Superabsorbent Polymers", Modern Superabsorbent Polymer Technology, ed. Buchholz, et al., 1988, pp. 69-117.

*Primary Examiner* — Edward M Johnson
(74) *Attorney, Agent, or Firm* — Marshall, Gerstein & Borun LLP

(57) ABSTRACT

Superabsorbent mixtures M comprising at least 70% by weight of superabsorbent A having a liquid absorption of 20 g/g (T20) of less than 300 s and/or a volumetric liquid absorption under pressure 0.3 psi (2.07 kPa) (VAUL) with a τ value of less than 400 s, and at least 5% by weight of superabsorbent B having a centrifuge retention capacity (CRC) of at least 30 g/g.

15 Claims, 6 Drawing Sheets

SUPERABSORBER MIXTURES

CROSS-REFERENCE TO RELATED APPLICATIONS

Figure 1:
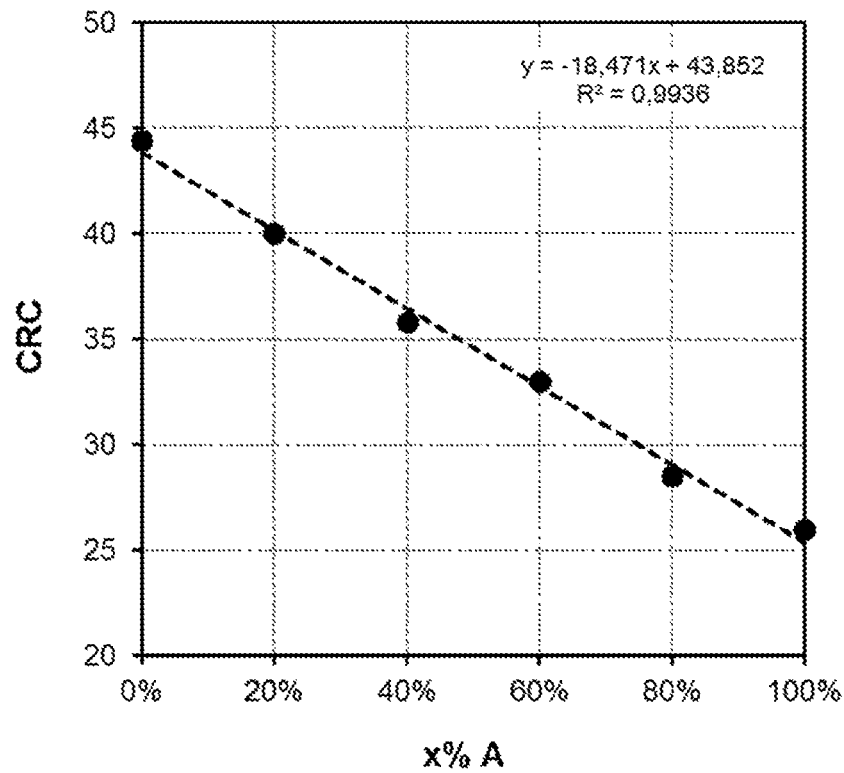

This is the U.S. national phase of International Application No. PCT/EP2019/050010, filed Jan. 2, 2019, which claims the benefit of European Patent Application No. 18150837.5, filed on Jan. 9, 2018.

The present invention relates to superabsorbent mixtures M comprising at least 70% by weight of superabsorbent A having a liquid absorption of 20 g/g (T20) of less than 300 s and/or a volumetric liquid absorption under pressure 0.3 psi (2.07 kPa) (VAUL) with a τ value of less than 400 s, and at least 5% by weight of superabsorbent B having a centrifuge retention capacity (CRC) of at least 30 g/g.

Superabsorbents are used to produce diapers, tampons, sanitary napkins and other hygiene articles, but also as water-retaining agents in market gardening. The superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

It was an object of the present invention to provide improved superabsorbents, especially superabsorbent mixtures having rapid liquid absorption and high centrifuge retention capacity.

The object was achieved by superabsorbent mixtures M comprising at least 70% by weight of superabsorbent A having a liquid absorption of 20 g/g (T20) of less than 300 s and/or a volumetric liquid absorption under pressure 0.3 psi (2.07 kPa) (VAUL) with a τ value of less than 400 s, and at least 5% by weight of superabsorbent B having a centrifuge retention capacity (CRC) of at least 30 g/g.

The liquid absorption of 20 g/g (T20) of superabsorbent A is preferably less than 240 s, more preferably less than 180 s, most preferably less than 120 s.

In the case of the volumetric liquid absorption under pressure 0.3 psi (2.07 kPa) (VAUL), the τ value is preferably less than 350 s, more preferably less than 250 s, most preferably less than 200 s.

The liquid absorption of 20 g/g (T20) and the volumetric liquid absorption under pressure 0.3 psi (2.07 kPa) (VAUL) of superabsorbent A can be improved by increasing the amount of crosslinker in the monomer solution. It is alternatively possible to extrude the polymer gel obtained in solution polymerization prior to drying, as described in WO 2014/118024 A1. It is additionally possible to increase the amount of surface postcrosslinker.

Superabsorbent A has a mean sphericity (mSPHT) of preferably less than 0.72, more preferably of less than 0.70, most preferably of less than 0.68.

Superabsorbent A has a bulk density (ASG) of preferably less than 0.70 g/ml, more preferably of less than 0.67 g/ml, most preferably of less than 0.64 g/ml.

Superabsorbent A is produced, for example, by solution polymerization. The resultant polymer gel has to be dried and comminuted. This leads to an irregular shape of the polymer particles and a relatively low bulk density (ASG). Superabsorbent A may alternatively also be produced by droplet polymerization or inverse suspension polymerization. Superabsorbent A has preferably been surface postcrosslinked.

The centrifuge retention capacity (CRC) of superabsorbent B is preferably at least 35 g/g, more preferably at least 40 g/g, most preferably at least 45 g/g.

The centrifuge retention capacity (CRC) of superabsorbent B can be improved by reducing the amount of crosslinker in the monomer solution. It is additionally possible to reduce the amount of surface postcrosslinker or to dispense with surface postcrosslinking.

Superabsorbent B has a mean sphericity (mSPHT) of preferably greater than 0.72, more preferably of greater than 0.76, most preferably of greater than 0.80.

Superabsorbent B has a bulk density (ASG) of preferably greater than 0.70 g/ml, more preferably of greater than 0.75 g/ml, most preferably of greater than 0.80 g/ml.

Superabsorbent B is produced, for example, by droplet polymerization. The resultant polymer particles have a substantially round shape and relatively high bulk density (ASG).

Superabsorbent B may alternatively also be produced by solution polymerization or inverse suspension polymerization. Superabsorbent B has preferably not been surface postcrosslinked.

Superabsorbent A and/or superabsorbent B has an average particle size of preferably 150 to 850 µm, more preferably of 200 to 600 µm, most preferably of 250 to 500 µm.

The present invention is based on the finding that the liquid absorption of 20 g/g (T20) and the volumetric liquid absorption under pressure 0.3 psi (2.07 kPa) (VAUL) behave in a nonlinear manner in superabsorbent mixtures. Superabsorbent mixtures comprising predominantly a superabsorbent having rapid liquid absorption of 20 g/g (T20) and/or rapid volumetric liquid absorption under pressure 0.3 psi (2.07 kPa) (VAUL) have a liquid absorption of 20 g/g (T20) or volumetric liquid absorption under pressure 0.3 psi (2.07 kPa) (VAUL) comparable to the pure superabsorbent. By contrast, the centrifuge retention capacity (CRC) behaves in a linear manner in superabsorbent mixtures. The centrifuge retention capacity (CRC) of a superabsorbent mixture can therefore be calculated by means of the centrifuge retention capacity (CRC) of the pure superabsorbents and the mixing ratio thereof.

If a superabsorbent A having a rapid liquid absorption of 20 g/g (T20) is mixed with a superabsorbent B having a high centrifuge retention capacity (CRC), the result is a superabsorbent mixture having a comparable liquid absorption of 20 g/g (T20) to the pure superabsorbent A and a distinctly increased centrifuge retention capacity (CRC) compared to the pure superabsorbent A.

If a superabsorbent A having a rapid volumetric liquid absorption under pressure 0.3 psi (2.07 kPa) (VAUL) is mixed with a superabsorbent B having a high centrifuge retention capacity (CRC), the result is a superabsorbent mixture having a comparable volumetric liquid absorption under pressure 0.3 psi (2.07 kPa) (VAUL) to the pure superabsorbent A and a distinctly increased centrifuge retention capacity (CRC) compared to the pure superabsorbent A.

The production of the superabsorbents is described in more detail hereinafter:

The superabsorbents can be produced by polymerizing a monomer solution or suspension comprising a) at least one ethylenically unsaturated monomer which bears acid groups and may have been at least partly neutralized,
b) at least one crosslinker and
c) at least one initiator, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monomethyl ether (MEHQ), as storage stabilizer.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monomethyl ether (MEHQ), based in each case on the unneutralized monomer a). For example, the monomer solution can be prepared by using an ethylenically unsaturated monomer bearing acid groups with an appropriate content of hydroquinone monomethyl ether (MEHQ).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b). Further suitable crosslinkers b) are the "nano-clays" described in US 2017/0361305, the waterglasses described in WO 00/31157 A1, and the aluminates described in WO 99/55767 A1.

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

The amount of crosslinker b) is preferably 0.25% to 1.5% by weight, more preferably 0.3% to 1.2% by weight and most preferably 0.4% to 0.8% by weight, calculated in each case on the basis of the total amount of monomer a) used. With rising crosslinker content, the centrifuge retention capacity (CRC) falls and the absorption under a pressure of 21.0 g/cm$^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Bruggemann Chemicals; Heilbronn; Germany). It is alternatively possible to use pure 2-hydroxy-2-sulfonatoacetic acid or a salt thereof as reducing component, especially when ascorbic acid is also used.

It is also possible to add chelate formers and 2-hydroxycarboxylic acids to the monomer solution before or during the polymerization, as described, for example, in WO 2017/170604 A1.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with solubility-exceeding monomer a), for example sodium acrylate. As the water content rises, the energy expenditure in the subsequent drying rises and, as the water content falls, the heat of polymerization can only be removed inadequately.

The acid groups of the resulting polymer gels have typically been partly neutralized. The neutralization is conducted at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

There follows an elucidation of solution polymerization:

Suitable reactors for solution polymerization are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted, for example in an extruder or kneader.

To improve the drying properties, the comminuted polymer gel obtained by means of a kneader can additionally be extruded.

The polymer gel is then typically dried with an air circulation belt drier until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is typically ground and classified, and the apparatus used for grinding may typically be single- or multistage roll mills, preferably two- or three-stage roll mills, pin mills, hammer mills or vibratory mills.

The average particle size of the polymer particles removed as the product fraction is preferably from 150 to 850 μm, more preferably from 250 to 600 μm, very particularly from 300 to 500 μm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 μm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably before, during or immediately after the polymerization, i.e. prior to the drying of the polymer gel. The excessively small polymer particles can be moistened with water and/or aqueous surfactant before or during the recycling.

It is also possible to remove excessively small polymer particles in later process steps, for example after the surface postcrosslinking or another coating step. In this case, the excessively small polymer particles recycled are surface postcrosslinked or coated in another way, for example with fumed silica.

If a kneading reactor is used for polymerization, the excessively small polymer particles are preferably added during the last third of the polymerization. However, it is also possible to incorporate the excessively small polymer particles into the polymer gel in a kneader or extruder connected downstream of the polymerization reactor.

If the excessively small polymer particles are added at a very early stage, for example actually to the monomer solution, this lowers the centrifuge retention capacity (CRC) of the resulting polymer particles. However, this can be compensated, for example, by adjusting the amount of crosslinker b) used.

The proportion of polymer particles having a particle size of at most 850 μm is preferably at least 90% by weight, more preferably at least 95% by weight, most preferably at least 98% by weight.

The proportion of polymer particles having a particle size of at most 600 μm is preferably at least 90% by weight, more preferably at least 95% by weight, most preferably at least 98% by weight.

Polymer particles of excessively large particle size lower the free swell rate. The proportion of excessively large polymer particles should therefore likewise be low. Excessively large polymer particles are therefore typically removed and recycled into the grinding.

There follows an elucidation of droplet polymerization:

In droplet polymerization, the monomer solution is metered into the reactor by means of at least one hole to form droplets. Droplet polymerization is described, for example, in WO 2014/079694 A1 and WO 2015/110321 A1.

The holes may, for example, be in a dropletizer plate. The number and size of the holes are selected according to the desired capacity and droplet size. The droplet diameter is typically 1.9 times the diameter of the hole. What is important here is that the liquid to be dropletized does not pass through the hole too rapidly and the pressure drop across the hole is not too great. Otherwise, the liquid is not dropletized, but rather the liquid jet is broken up (sprayed) owing to the high kinetic energy. The Reynolds number based on the throughput per hole and the hole diameter is preferably less than 2000, more preferably less than 1600, especially preferably less than 1400 and most preferably less than 1200.

The dropletizer plate has preferably at least 5, more preferably at least 25 and most preferably at least 50 holes, and preferably up to 750, more preferably up to 500 and most preferably up to 250 holes. The diameter of the holes is selected according to the desired droplet size.

The diameter of the holes is preferably from 50 to 500 μm, more preferably from 70 to 300 μm and most preferably from 100 to 200 μm. The distance between the holes is preferably 50 to 500 times, more preferably 70 to 300 times, most preferably 80 to 200 times, the hole diameter. Excessively small distances lead to formation of agglomerates; excessively large distances reduce the yield.

The temperature of the monomer solution on passage through the holes is preferably from 5 to 80° C., more preferably from 10 to 70° C. and most preferably from 30 to 60° C.

A carrier gas flows through the reactor. This carrier gas can be conducted through the reactor in cocurrent or in countercurrent to the free-falling droplets of the monomer solution, preferably in cocurrent, i.e. from the bottom upward. After one pass, the carrier gas is preferably recycled at least partly into the reactor as cycle gas, preferably to an extent of at least 50% and more preferably to an extent of at least 75%. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume and most preferably from 2 to 7% by volume.

As well as oxygen, the carrier gas preferably comprises nitrogen. The nitrogen content of the carrier gas is preferably at least 80% by volume, more preferably at least 90% by volume and most preferably at least 95% by volume. It is also possible to use gas mixtures. The carrier gas may also be laden with steam and/or acrylic acid vapors.

The gas velocity is preferably set such that the flow in the reactor is directed, for example no convection currents opposed to the general flow direction are present, and is typically 0.1 to 2.5 m/s, preferably 0.3 to 1.5 m/s, more preferably from 0.5 to 1.2 m/s, especially preferably 0.6 to 1.0 m/s and most preferably 0.7 to 0.9 m/s.

The carrier gas flowing through the reactor is appropriately preheated to the reaction temperature upstream of the reactor.

Advantageously, the gas inlet temperature is regulated such that the gas outlet temperature, i.e. the temperature with which the carrier gas leaves the reactor, is typically from 90 to 150° C., preferably from 100 to 140° C., more preferably from 105 to 135° C., especially preferably from 110 to 130° C. and most preferably from 115 to 125° C.

The reaction can be performed under elevated pressure or under reduced pressure; a reduced pressure of down to 100 mbar relative to ambient pressure is preferred.

The reaction offgas, i.e. the gas leaving the reactor, can, for example, be cooled in a heat exchanger. This condenses water and unconverted monomer a). Thereafter, the reaction offgas can at least partly be reheated and recycled into the reactor as cycle gas. A portion of the reaction offgas can be discharged and replaced by fresh carrier gas, in which case water and unconverted monomers a) present in the reaction offgas can be removed and recycled.

Particular preference is given to an integrated heating system, which means that some of the waste heat in the cooling of the offgas is used to heat the cycle gas.

The reactors may be trace-heated. The trace heating is adjusted such that the wall temperature is at least 5° C. above the internal reactor temperature, and condensation at the reactor walls is reliably prevented.

There follows a description of inverse suspension polymerization:

Inverse suspension polymerization involves suspending the monomer solution in a hydrophobic solvent during the polymerization. Inverse suspension polymerization is described, for example, in WO 2008/068208 A1 and WO 2015/062883 A2.

Usable hydrophobic solvents are all the solvents known to the person skilled in the art for use in suspension polymerization. Preference is given to using aliphatic hydrocarbons, such as n-hexane, n-heptane, n-octane, n-nonane, n-decane, cyclohexane or mixtures thereof. Hydrophobic solvents have a solubility in water at 23° C. of less than 5 g/100 g, preferably less than 1 g/100 g, more preferably less than 0.5 g/100 g.

The hydrophobic solvent boils within the range from preferably 50 to 150° C., more preferably 60 to 120° C., most preferably 70 to 90° C.

The ratio between hydrophobic solvent and monomer solution is 0.5 to 3, preferably 0.7 to 2.5 and very preferably from 0.8 to 2.2.

The mean diameter of the monomer solution droplets in the suspension, if no agglomeration is conducted, is preferably at least 100 μm, more preferably from 100 to 1000 μm, more preferably from 150 to 850 μm, most preferably from 300 to 600 μm, the droplet diameter being determinable by light scattering and signifying the volume-average mean diameter.

The diameter of the monomer solution droplets can be adjusted via the stirrer energy introduced and through suitable dispersing aids.

For dispersion of the aqueous monomer solution in the hydrophobic solvent or for dispersion of the resultant superabsorbent particles, preference is given to adding dispersing aids. These dispersing aids may be anionic, cationic, nonionic or amphoteric surfactants, or natural, semisynthetic or synthetic polymers.

Anionic surfactants are, for example, sodium polyoxyethylene dodecyl ether sulfate and sodium dodecyl ether sulfate. A cationic surfactant is, for example, trimethylstearylammonium chloride. An amphoteric surfactant is, for example, carboxymethyldimethylcetylammonium. Nonionic surfactants are, for example, sucrose fatty acid esters, such as sucrose monostearate and sucrose dilaurate, sorbitan esters such as sorbitan monostearate, polyoxyalkylene compounds based on sorbitan esters, such as polyoxyethylenesorbitan monostearate.

The dispersing aid is typically dissolved or dispersed in the hydrophobic solvent. The dispersing aid is used in amounts between 0.01 and 10% by weight, preferably between 0.2 and 5% by weight, more preferably between 0.5 and 2% by weight, based on the monomer solution. The diameter of the monomer solution droplets can be adjusted via the type and amount of dispersing aid.

Advantageously, several stirred reactors are connected in series for the polymerization. Through postreaction in further stirred reactors, the monomer conversion can be increased and backmixing can be reduced. In this context, it is additionally advantageous when the first stirred reactor is not too large. With increasing size of the stirred reactor, there is inevitably broadening of the size distribution of the dispersed monomer solution droplets. A relatively small first reactor therefore enables the production of superabsorbent particles with a particularly narrow particle size distribution.

The reaction is preferably conducted under reduced pressure, for example at a pressure of 800 mbar. The pressure can be used to set the boiling point of the reaction mixture to the desired reaction temperature.

If the polymerization is conducted under adequate reflux, the inertization can be dispensed with. In this case, the dissolved oxygen is removed from the polymerization reactor together with the evaporating solvent.

The superabsorbent particles may be azeotropically dewatered in the polymer dispersion and separated from the polymer dispersion, and the separated superabsorbent particles may be dried to remove the adhering residual hydrophobic solvent.

There follows a description of surface postcrosslinking:

To further improve the properties, the polymer particles can be thermally surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, β-hydroxyalkylamides, as described in DE 102 04 938 A1 and U.S. Pat. No. 6,239,230, or oxazolines, as described in EP 0 999 938 A2.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, oxetanes in EP 2 204 388 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and butane-1,4-diol.

Very particularly preferred surface postcrosslinkers are 2-hydroxyethyl-2-oxazolidinone, 2-oxazolidinone and propane-1,3-diol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers have a vertically mounted mixing shaft. Suitable mixers are, for example, horizontal Pflugschar® plowshare mixers (Gebr. LÖdige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, propane-1,3-diol/water, propylene glycol/water, 2-methylpropane-1,3-diol/water, ethylene glycol/water, diethylene glycol/water, triethylene glycol/water, tetraethylene glycol/water, or polyethylene glycol/water, where the mass mixing ratio is preferably from 20:80 to 40:60.

The surface postcrosslinking is preferably performed in contact dryers, more preferably paddle dryers, most preferably disk dryers. Suitable dryers are, for example, Hosokawa Bepex® Horizontal Paddle Dryer (Hosokawa Micron GmbH; Leingarten; Germany), Hosokawa Bepex® Disk Dryer (Hosokawa Micron GmbH; Leingarten; Germany), Holo-Flite® dryers (Metso Minerals Industries Inc.; Danville; USA) and Nara Paddle Dryer (NARA Machinery Europe; Frechen; Germany). Moreover, fluidized bed dryers may also be used.

The surface postcrosslinking can be effected in the mixer itself, by heating the jacket or blowing in warm air. Equally suitable is a downstream dryer, for example a tray dryer, a rotary tube oven or a heatable screw. It is particularly advantageous to effect mixing and thermal surface postcrosslinking in a fluidized bed dryer.

Preferred reaction temperatures are in the range of 100 to 250° C., preferably 120 to 220° C., more preferably 130 to 210° C., most preferably 150 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disk Cooler (Hosokawa Micron GmbH; Leingarten; Germany), Holo-Flite®coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

To further improve the properties, the polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging.

Suitable coatings for improving the free swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

Methods:

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, N.C. 27518, USA, www.inda.org). This publication is obtainable both from EDANA and from INDA.

The measurements should, unless stated otherwise, be conducted at an ambient temperature of 23±2° C. and a relative air humidity of 50±10%. The superabsorbent particles are mixed thoroughly before the measurement.

Liquid Absorption of 20 g/g (T20)

Liquid absorption of 20 g/g (T20) is determined by the "K(t) Test Method (Dynamic Effective Permeability and Uptake Kinetics Measurement Test Method)" described in EP 2 535 027 A1 on pages 13 to 18.

Volumetric Absorption of Liquid Under a Pressure of 0.3 Psi (2.07 kPa) (VAUL)

For the volumetric absorption of liquid under a pressure of 0.3 psi (2.07 kPa) (VAUL), the r value is determined by the test method "Volumetric Absorbency Under Load (VAUL)" described in WO 2014/079694 A1 on pages 39 and 40. The r value is described therein as the "characteristic swelling time".

Residual Monomers

The residual monomer content is determined by EDANA recommended test method No. WSP 210.2 (05) "Residual Monomers".

Moisture Content

Moisture content is determined by EDANA recommended test method No. WSP 230.2 (05) "Mass Loss Upon Heating".

Free Swell Capacity

Free swell capacity (FSC) is determined by EDANA recommended test method No. WSP 240.2 (05) "Free Swell Capacity in Saline, Gravimetric Determination".

Centrifuge Retention Capacity

Centrifuge retention capacity (CRC) is determined by EDANA recommended test method No. WSP 241.2 (05) "Fluid Retention Capacity in Saline, After Centrifugation".

Absorption Under a Pressure of 0.0 q/Cm$^2$ (Absorption Under No Load)

Absorption under a pressure of 0.0 g/cm$^2$ (AUNL) is determined analogously to EDANA recommended test method No. WSP 242.2 (05) "Absorption Under Pressure, Gravimetric Determination", except that a pressure of 0.0 g/cm$^2$ (0.0 psi) is established rather than a pressure of 21.0 g/cm$^2$ (0.3 psi).

Absorption Under a Pressure of 21.0 q/Cm$^2$ (Absorption Under Load)

Absorption under a pressure of 21.0 g/cm$^2$ (AUL) is determined by EDANA recommended test method No. WSP 242.2 (05) "Absorption Under Pressure, Gravimetric Determination".

Absorption Under a Pressure of 49.2 q/Cm$^2$ (Absorption Under High Load)

Absorption under a pressure of 49.2 g/cm$^2$ (AUHL) is determined analogously to EDANA recommended test method No. WSP 242.2 (05) "Absorption Under Pressure, Gravimetric Determination", except that a pressure of 49.2 g/cm$^2$ (0.7 psi) is established rather than a pressure of 21.0 g/cm$^2$ (0.3 psi).

Extractables

The content of extractables in the superabsorbent particles is determined by EDANA recommended test method No. WSP 270.2 (05) "Extractable".

Saline Flow Conductivity

Figure 8:
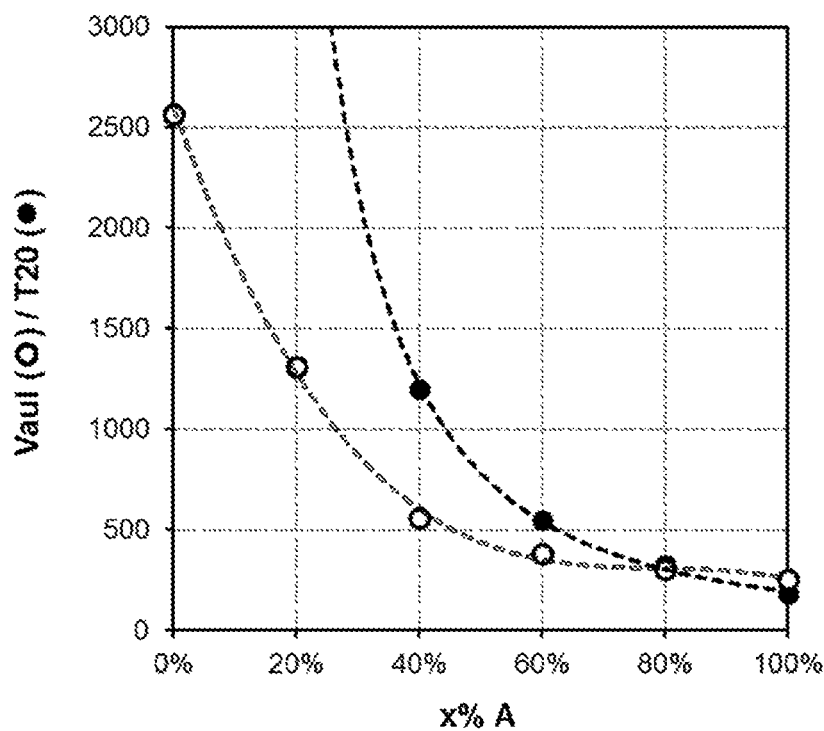

The saline flow conductivity (SFC) of a swollen gel layer under a pressure of 0.3 psi (2070 Pa) is, as described in EP 0 640 330 A1, determined as the gel layer permeability of a swollen gel layer of superabsorbent particles, the apparatus described on page 19 and in FIG. 8 in the cited patent application having been modified such that the glass frit (40) is no longer used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

Saline flow conductivity (SFC) is calculated as follows:

$$\text{SFC } [\text{cm}^3\text{s/g}] = (Fg(t=0) \times L_0)/(d \times A \times WP)$$

where Fg(t=0) is the flow of NaCl solution in g/s, which is obtained using linear regression analysis of the Fg(t) data of the flow determinations by extrapolation to t=0, $L_0$ is the thickness of the gel layer in cm, d is the density of the NaCl solution in g/cm$^3$, A is the area of the gel layer in cm$^2$, and WP is the hydrostatic pressure over the gel layer in dyn/cm$^2$.

Vortex Test 50.0 ml±1.0 ml of a 0.9% by weight aqueous sodium chloride solution are introduced into a 100 ml beaker which comprises a magnetic stirrer bar of size 30 mm×6 mm. A magnetic stirrer is used to stir the sodium chloride solution at 600 rpm. Then 2.000 g±0.010 g of superabsorbent particles is added as rapidly as possible, and the time taken for the stirrer vortex to disappear as a result of the absorption of the sodium chloride solution by the superabsorbent particles is measured. When measuring this time, the entire contents of the beaker may still be rotating as a homogeneous gel mass, but the surface of the gelated sodium chloride solution must no longer exhibit any individual turbulences. The time taken is reported as the vortex.

Mean Sphericity (mSPHT)

Mean sphericity (mSPHT) is determined with the ParTan® 3001 L particle analyzer (Microtrac Europe GmbH; Germany).

The sample to be analyzed is introduced into a funnel. The computer-controlled measurement system starts the metering device and ensures a continuous, concentration-regulated particle flow. The particles fall individually through the measurement shaft and generate high-contrast shadow images between light source and high-resolution camera. The light source is actuated by the camera and, because of very short exposure times, produces faultless image information for the multiple evaluation of each individual particle in real time.

In a 3D process, each particle is analyzed repeatedly and the process thus gives the absolute results for length, width, thickness, area and circumference. The number of pixels covered by the particle is used to calculate the size and shape.

Bulk Density

Bulk density (ASG) is determined by EDANA recommended test method No. WSP 260.2 (05) "Density, Gravimetric Determination".

Average Particle Size

Average particle size is determined by means of EDANA recommended test method No. WSP 220.2 (05) "Particle Size Distribution", by plotting the proportions by mass of the screen fractions in cumulated form and determining the average particle size from the graph. The average particle size here is the value of the mesh size which arises for a cumulative 50% by weight.

EXAMPLES

Production Example 1—Superabsorbent B

A base polymer was produced analogously to example 1 of WO 2017/207330 A1. The neutralization level was 72.0 mol %, and the solids content of the monomer solution was 43.0% by weight.

The polyunsaturated crosslinker used was 3-tuply ethoxylated glycerol triacrylate. The crosslinker was prepared according to example 7 of WO 03/104299 A1. The crosslinker was used in an amount of 0.20% by weight, based on acrylic acid prior to neutralization. In addition, the monomer solution comprised 0.75% by weight of polyethylene glycol-4000 (polyethylene glycol having an average molar mass of 4000 g/mol), again based on acrylic acid prior to neutralization.

Polymerization initiators used were 0.16% by weight of sodium peroxodisulfate, 0.0007% by weight of hydrogen peroxide and 0.0028% by weight of ascorbic acid, based in each case on acrylic acid prior to neutralization.

The superabsorbent (base polymer) produced had a centrifuge retention capacity (CRC) of 44.8 g/g, an absorption under a pressure of 0.0 g/cm$^2$ (AUNL) of 48.2 g/g, an absorption under a pressure of 21.0 g/cm$^2$ (AUL) of 7.8 g/g, a free swell capacity (FSC) of 56.9 g/g, a moisture content of 3.2% by weight and a bulk density (ASG) of 0.67 g/ml.

The superabsorbent had the following particle size distribution:

| | |
|---|---|
| >710 μm | 0.2% by weight |
| 600-710 μm | 14.3% by weight |
| 500-600 μm | 19.0% by weight |
| 400-500 μm | 28.8% by weight |
| 300-400 μm | 19.0% by weight |
| 200-300 μm | 12.3% by weight |
| 150-200 μm | 5.2% by weight |
| 106-150 μm | 1.2% by weight |
| <106 μm | 0.0% by weight |

The superabsorbent had a median particle size (d50) of 430 μm and a mean sphericity (mSPHT) of 0.60.

Production Example 2—Superabsorbent B 1200 g of the base polymer from production example 1 was introduced into a Pflugschar® M5 plowshare mixer with heating jacket (Gebr. Lödige Maschinenbau GmbH, Paderborn, Germany) and coated at 23° C. and a shaft speed of 200 revolutions per minute by means of a two-phase spray nozzle with the following solution, based in each case on the base polymer:

0.04% by weight of ethylene glycol diglycidyl ether
1.5% by weight of propylene glycol
0.05% by weight of aluminum sulfate
3.0% by weight of water The shaft speed was set to 60 revolutions per minute and the product was brought to a temperature of 120° C. In order to maintain this temperature, the temperature of the heating fluid was reduced appropriately. After 30 minutes at 120° C., the sample was cooled to ambient temperature.

Subsequently, the polymer particles obtained were remoisturized in a further mixer at 80° C. For this purpose, 7.0% by weight of a 0.05% by weight aqueous aluminum sulfate solution was sprayed onto the polymer by means of a nitrogen-operated two-phase nozzle and while stirring. While stirring, the polymer was cooled down to 25° C. within 20 minutes and sieved off to a particle size of 150 to 710 μm.

The superabsorbent produced had a centrifuge retention capacity (CRC) of 33.4 g/g, an absorption under a pressure of 0.0 g/cm$^2$ (AUNL) of 48.3 g/g, an absorption under a pressure of 21.0 g/cm$^2$ (AUL) of 31.7 g/g, an absorption under a pressure of 49.2 g/cm$^2$ (AUHL) of 23.9 g/g, a free swell capacity (FSC) of 54.4 g/g, a moisture content of 5.0% by weight, a saline flow conductivity (SFC) of $8\times10^{-7}$ cm$^3$ s/g, a vortex of 52 s, a residual monomer content of 310 ppm and a bulk density (ASG) of 0.67 g/ml.

The superabsorbent had the following particle size distribution:

| | |
|---|---|
| >710 μm | 0.50% by weight |
| 600-710 μm | 11.2% by weight |
| 500-600 μm | 20.9% by weight |
| 425-500 μm | 24.5% by weight |
| 300-425 μm | 23.6% by weight |
| 150-300 μm | 18.0% by weight |
| 106-150 μm | 0.4% by weight |
| <106 μm | 0.0% by weight |

The superabsorbent had a median particle size (d50) of 464 μm and a mean sphericity (mSPHT) of 0.60.

Production Example 3—Superabsorbent A

A superabsorbent was produced according to example 14 of WO 2014/118024 A1. The superabsorbent produced had a bulk density (ASG) of 0.60 g/ml, a centrifuge retention capacity (CRC) of 26.0 g/g, an absorption under a pressure of 49.2 g/cm$^2$ (AUHL) of 23.9 g/g and a saline flow conductivity (SFC) of $136\times10^{-7}$ cm$^3$ s/g.

The superabsorbent had the following particle size distribution:

| | |
|---|---|
| >710 μm | 8.7% by weight |
| 600-710 μm | 19.2% by weight |
| 500-600 μm | 26.9% by weight |
| 400-500 μm | 21.9% by weight |
| 300-400 μm | 14.2% by weight |
| 150-300 μm | 9.0% by weight |
| 106-150 μm | 0.1% by weight |
| <106 μm | 0.0% by weight |

The superabsorbent had a median particle size (d50) of 510 μm and a mean sphericity (mSPHT) of 0.66.

Production Example 4—Superabsorbent B

A superabsorbent was produced analogously to example 2 of WO 2016/134905 A1. The monomer solution used additionally comprised 1.07% by weight of the disodium salt of 1-hydroxyethylidene-1,1-diphosphonic acid.

The gas inlet temperature of reaction zone (5) was 167° C., the gas outlet temperature of reaction zone (5) was 107° C., the gas inlet temperature of the internal fluidized bed (27) was 100° C., the product temperature in the internal fluidized bed (27) was 78° C., the gas outlet temperature of the condensation column (12) was 57° C., and the gas outlet temperature of the gas drying unit (37) was 47° C.

The superabsorbent produced (base polymer) had a bulk density (ASG) of 0.681 g/ml, a centrifuge retention capacity (CRC) of 56.8 g/g, an absorption under a pressure of 21.0 g/cm$^2$ (AUL) of 8.1 g/g, a residual monomer content of 8550 ppm, an extractables content of 9.7% by weight and a moisture content of 8.5% by weight.

The superabsorbent had the following particle size distribution:

| | |
|---|---|
| >1000 μm | 0.3% by weight |
| 850-1000 μm | 1.1% by weight |
| 600-850 μm | 4.7% by weight |
| 500-600 μm | 13.9% by weight |
| 400-500 μm | 35.5% by weight |
| 300-400 μm | 34.3% by weight |
| 250-300 μm | 6.6% by weight |
| 200-250 μm | 3.1% by weight |
| 106-200 μm | 0.4% by weight |
| <106 μm | 0.1% by weight |

The superabsorbent had a median particle size (d50) of 397 μm and a mean sphericity (mSPHT) of 0.81.

The base polymer was subsequently surface postcrosslinked analogously to examples 11 to 15 of WO 2015/110321 A1. 2.0% by weight of ethylene carbonate, 5.0% by weight of water and 0.4% by weight of aluminum sulfate were used, based in each case on the base polymer. The product temperature was 150° C. and the height of the weir was 75%.

In the cooler downstream of the surface postcrosslinking, 4.7% by weight of a 0.1% by weight aqueous solution of sorbitan monolaurate was added.

The superabsorbent produced had a bulk density (ASG) of 0.753 g/ml, a centrifuge retention capacity (CRC) of 46.8 g/g, an absorption under a pressure of 21.0 g/cm$^2$ (AUL) of 33.0 g/g, an absorption under a pressure of 49.2 g/cm$^2$ (AUHL) of 16.7 g/g, a saline flow conductivity (SFC) of 0×10$^{-7}$ cm$^3$ s/g, a vortex of 60 s, a moisture content of 4.4% by weight, a residual monomer content of 460 ppm and an extractables content of 5.0% by weight.

The surface postcrosslinked superabsorbent had the following particle size distribution:

| | |
|---|---|
| >850 μm | 0.0% by weight |
| 710-850 μm | 0.6% by weight |
| 600-710 μm | 4.5% by weight |
| 500-600 μm | 10.9% by weight |
| 400-500 μm | 40.6% by weight |
| 300-400 μm | 34.0% by weight |
| 250-300 μm | 6.1% by weight |
| 200-250 μm | 2.6% by weight |
| 150-200 μm | 0.5% by weight |
| <150 μm | 0.2% by weight |

The superabsorbent had a median particle size (d50) of 405 μm and a mean sphericity (mSPHT) of 0.80.

Production Example 5—Superabsorbent A

A superabsorbent was produced analogously to example 2 of WO 2016/134905 A1. The monomer solution used additionally comprised 1.07% by weight of the disodium salt of 1-hydroxyethylidene-1,1-diphosphonic acid. Also used was a dropletizer plate with 645 holes, a hole diameter of 100 μm and a hole separation of 8 mm.

The gas inlet temperature of reaction zone (5) was 167° C., the gas outlet temperature of reaction zone (5) was 108° C., the gas inlet temperature of the internal fluidized bed (27) was 94° C., the product temperature in the internal fluidized bed (27) was 73° C., the gas outlet temperature of the condensation column (12) was 58° C., and the gas outlet temperature of the gas drying unit (37) was 47° C.

The superabsorbent produced (base polymer) had a bulk density (ASG) of 0.648 g/ml, a centrifuge retention capacity (CRC) of 54.7 g/g, an absorption under a pressure of 21.0 g/cm$^2$ (AUL) of 8.8 g/g, a residual monomer content of 12600 ppm, an extractables content of 8.9% by weight and a moisture content of 9.0% by weight.

The superabsorbent had the following particle size distribution:

| | |
|---|---|
| >1000 μm | 0.1% by weight |
| 850-1000 μm | 0.1% by weight |
| 600-850 μm | 0.6% by weight |
| 500-600 μm | 2.6% by weight |
| 400-500 μm | 13.1% by weight |
| 300-400 μm | 41.5% by weight |
| 250-300 μm | 22.0% by weight |
| 200-250 μm | 15.0% by weight |
| 106-200 μm | 4.9% by weight |
| <106 μm | 0.1% by weight |

The superabsorbent had a median particle size (d50) of 284 μm and a mean sphericity (mSPHT) of 0.82.

The base polymer was subsequently surface postcrosslinked analogously to examples 11 to 15 of WO 2015/110321 A1. 2.0% by weight of ethylene carbonate, 5.0% by weight of water and 0.4% by weight of aluminum sulfate were used, based in each case on the base polymer. The product temperature was 175° C. and the height of the weir was 75%.

In the cooler downstream of the surface postcrosslinking, 4.7% by weight of a 0.1% by weight aqueous solution of sorbitan monolaurate was added.

The superabsorbent produced had a bulk density (ASG) of 0.733 g/ml, a centrifuge retention capacity (CRC) of 28.6 g/g, an absorption under a pressure of 21.0 g/cm$^2$ (AUL) of 29.2 g/g, an absorption under a pressure of 49.2 g/cm$^2$ (AUHL) of 23.8 g/g, a saline flow conductivity (SFC) of 32×10$^{-7}$ cm$^3$ s/g, a vortex of 43 s, a moisture content of 3.5% by weight, a residual monomer content of 790 ppm and an extractables content of 1.5% by weight.

The surface postcrosslinked superabsorbent had the following particle size distribution:

| | |
|---|---|
| >850 μm | 0.2% by weight |
| 710-850 μm | 0.2% by weight |
| 600-710 μm | 0.9% by weight |
| 500-600 μm | 2.1% by weight |
| 400-500 μm | 13.5% by weight |
| 300-400 μm | 41.9% by weight |
| 250-300 μm | 24.2% by weight |
| 200-250 μm | 11.8% by weight |
| 150-200 μm | 4.7% by weight |
| <150 μm | 0.5% by weight |

The superabsorbent had a median particle size (d50) of 285 μm and a mean sphericity (mSPHT) of 0.80.

Production Example 6—Superabsorbent B

A superabsorbent of the AQUA KEEP SA-60-SX-II type was used (Sumitomo Seika Chemicals Co., Ltd.; Osaka; Japan). AQUA KEEP SA-60-SX-II is a superabsorbent produced by inverse suspension polymerization.

The superabsorbent had a bulk density (ASG) of 0.66 g/ml, a centrifuge retention capacity (CRC) of 34.0 g/g, an absorption under a pressure of 0.0 g/cm$^2$ (AUNL) of 54.8 g/g, an absorption under a pressure of 21.0 g/cm$^2$ (AUL) of 32.8 g/g, an absorption under a pressure of 49.2 g/cm$^2$ (AUHL) of 14.7 g/g, a saline flow conductivity (SFC) of 0×10$^{-7}$ cm$^3$ s/g, a vortex of 46 s and a moisture content of 11.1% by weight.

The superabsorbent had the following particle size distribution:

| | |
|---|---|
| >710 μm | 6.5% by weight |
| 600-710 μm | 9.6% by weight |
| 500-600 μm | 16.1% by weight |
| 400-500 μm | 24.7% by weight |
| 300-400 μm | 28.2% by weight |
| 150-300 μm | 14.6% by weight |
| 106-150 μm | 0.3% by weight |
| <106 μm | 0.0% by weight |

The superabsorbent had a median particle size (d50) of 429 μm and a mean sphericity (mSPHT) of 0.68.

Superabsorbent A and superabsorbent B were mixed in different ratios, and the superabsorbent mixtures M obtained were analyzed. The results are compiled in tables 1 to 6:

TABLE 1

Mixtures of superabsorbent A (example 3) and superabsorbent B (example 1)

| Example | Superabsorbent B | Superabsorbent A | CRC g/g | T20 s | VAUL s |
|---|---|---|---|---|---|
| 1*) | 100% | 0% | 44.4 | >1200 | 2567 |
| 2*) | 80% | 20% | 40.0 | >1200 | 1330 |
| 3*) | 60% | 40% | 35.8 | >1200 | 386 |
| 4*) | 40% | 60% | 33.0 | 393 | 243 |

TABLE 1-continued

Mixtures of superabsorbent A (example 3) and superabsorbent B (example 1)

| Example | Superabsorbent B | Superabsorbent A | CRC g/g | T20 s | VAUL s |
|---|---|---|---|---|---|
| 5 | 20% | 80% | 28.5 | 210 | 179 |
| 6*) | 0% | 100% | 26.0 | 165 | 180 |

*)comparative example

Figure 2:
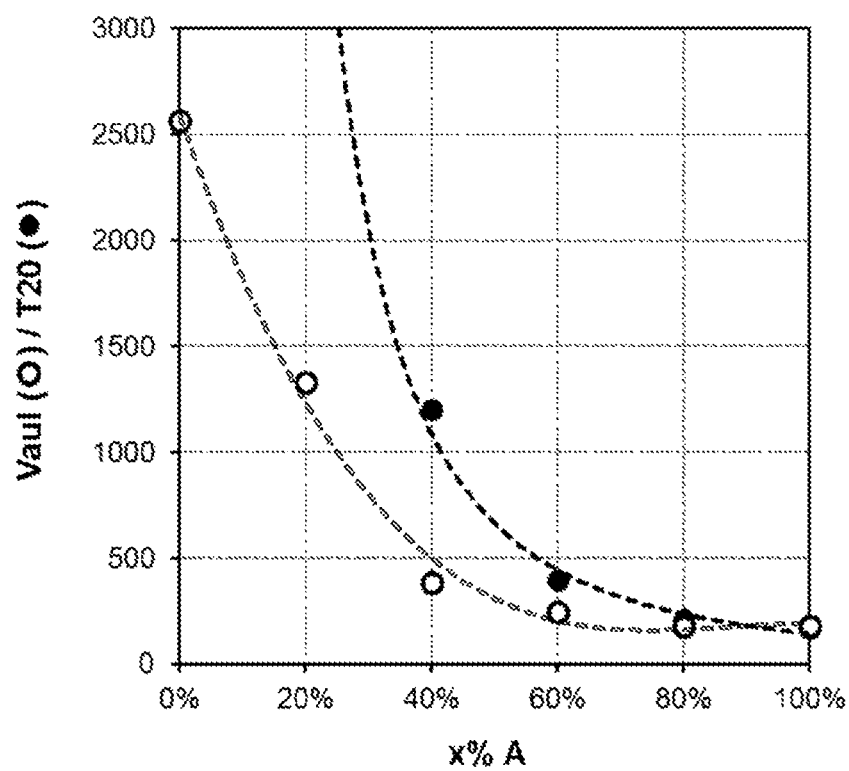

The results of table 1 are shown in FIGS. 1 and 2.

TABLE 2

Mixtures of superabsorbent A (example 5) and superabsorbent B (example 4)

| Example | Superabsorbent B | Superabsorbent A | CRC g/g | T20 s | VAUL s |
|---|---|---|---|---|---|
| 7*) | 100% | 0% | 46.8 | >1200 | 887 |
| 8*) | 80% | 20% | 44.3 | 749 | 762 |
| 9*) | 60% | 40% | 39.6 | 396 | 689 |
| 10*) | 40% | 60% | 36.5 | 300 | 470 |
| 11 | 20% | 80% | 31.6 | 220 | 365 |
| 12*) | 0% | 100% | 28.6 | 182 | 254 |

*)comparative example

Figure 3:
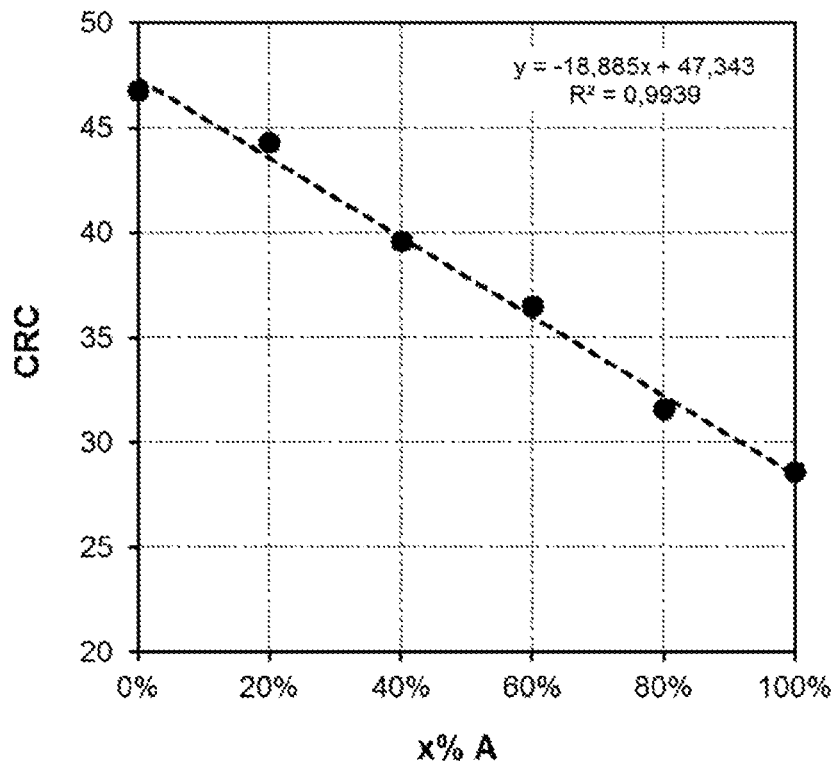
Figure 4:
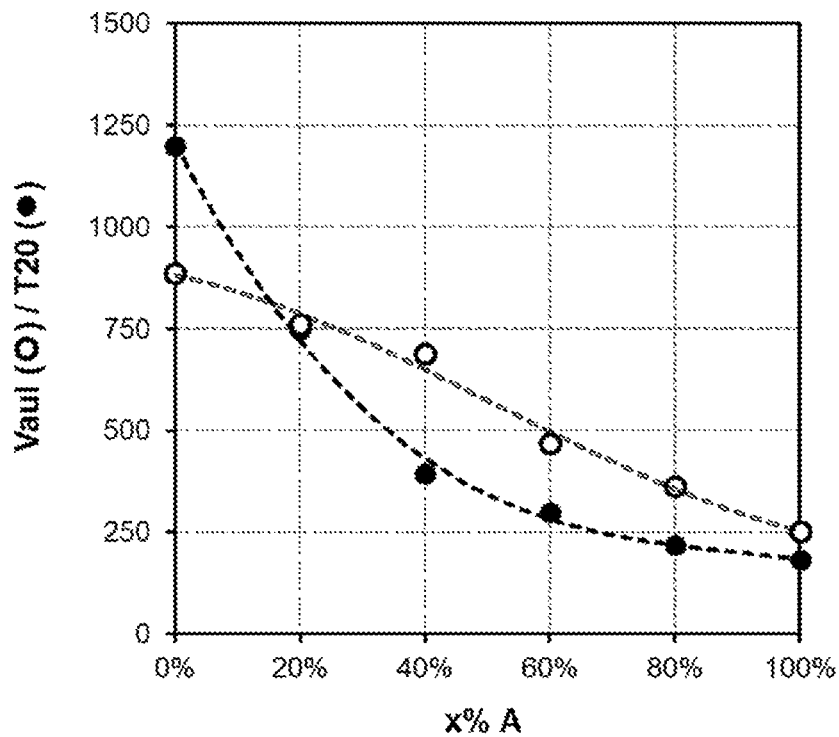

The results of table 2 are shown in FIGS. 3 and 4.

TABLE 3

Mixtures of superabsorbent A (example 3) and superabsorbent B (example 4)

| Example | Superabsorbent B | Superabsorbent A | CRC g/g | T20 s | VAUL s |
|---|---|---|---|---|---|
| 13*) | 100% | 0% | 46.8 | >1200 | 887 |
| 14*) | 80% | 20% | 41.8 | 563 | 614 |
| 15*) | 60% | 40% | 37.6 | 317 | 422 |
| 16*) | 40% | 60% | 32.8 | 228 | 303 |
| 17 | 20% | 80% | 28.5 | 187 | 206 |
| 18*) | 0% | 100% | 26.0 | 165 | 180 |

*)comparative example

Figure 5:
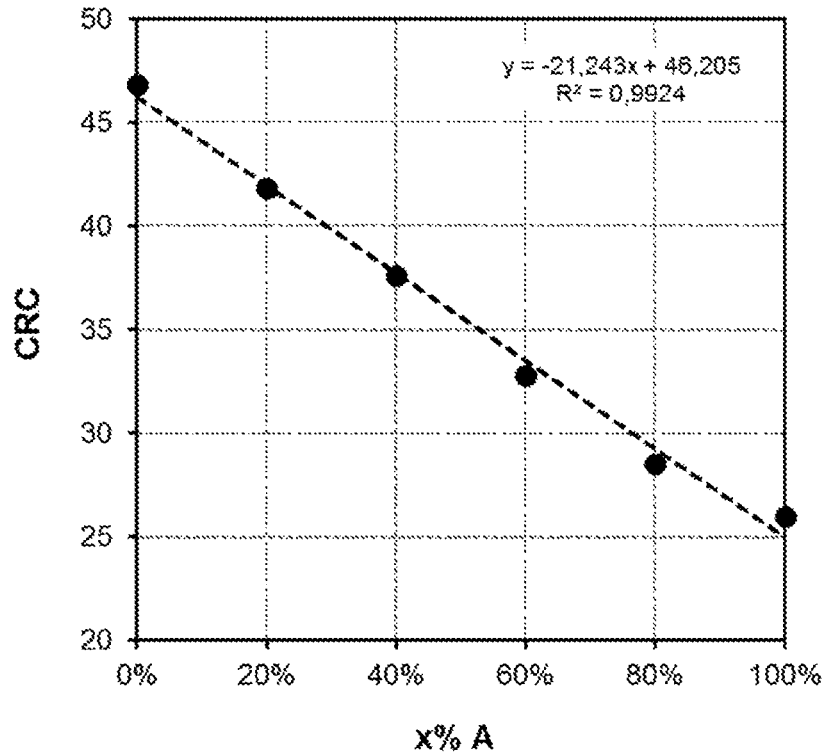
Figure 6:
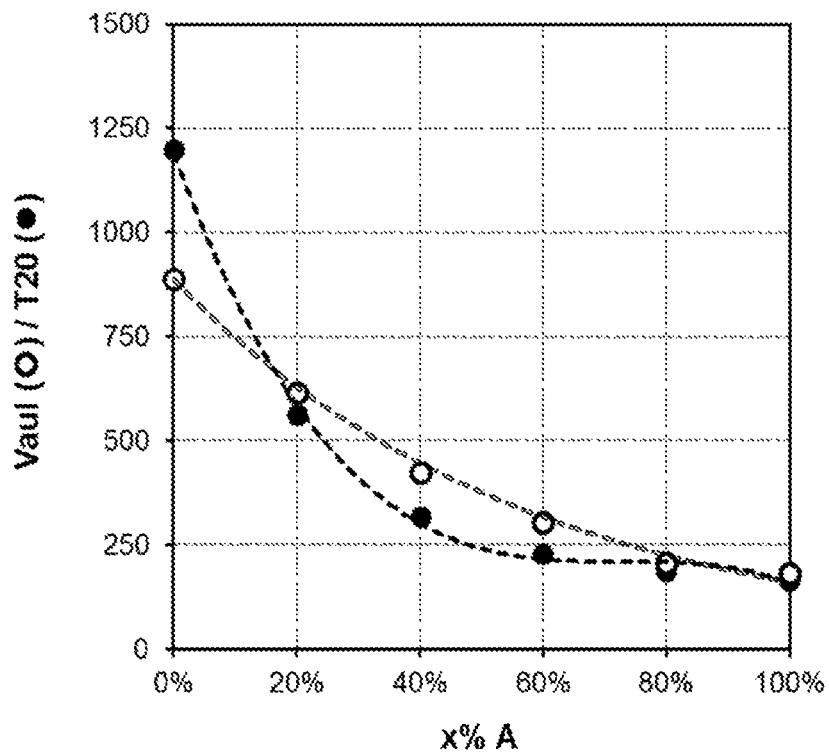

The results of table 3 are shown in FIGS. 5 and 6.

TABLE 4

Mixtures of superabsorbent A (example 5) and superabsorbent B (example 1)

| Example | Superabsorbent B | Superabsorbent A | CRC g/g | T20 s | VAUL s |
|---|---|---|---|---|---|
| 19*) | 100% | 0% | 44.4 | >1200 | 2567 |
| 20*) | 80% | 20% | 41.0 | >1200 | 1309 |
| 21*) | 60% | 40% | 38.4 | >1200 | 561 |

TABLE 4-continued

Mixtures of superabsorbent A (example 5) and superabsorbent B (example 1)

| Example | Superabsorbent B | Superabsorbent A | CRC g/g | T20 s | VAUL s |
|---|---|---|---|---|---|
| 22*) | 40% | 60% | 34.0 | 546 | 378 |
| 23 | 20% | 80% | 30.7 | 323 | 300 |
| 24*) | 0% | 100% | 28.6 | 182 | 254 |

*)comparative example

Figure 7:
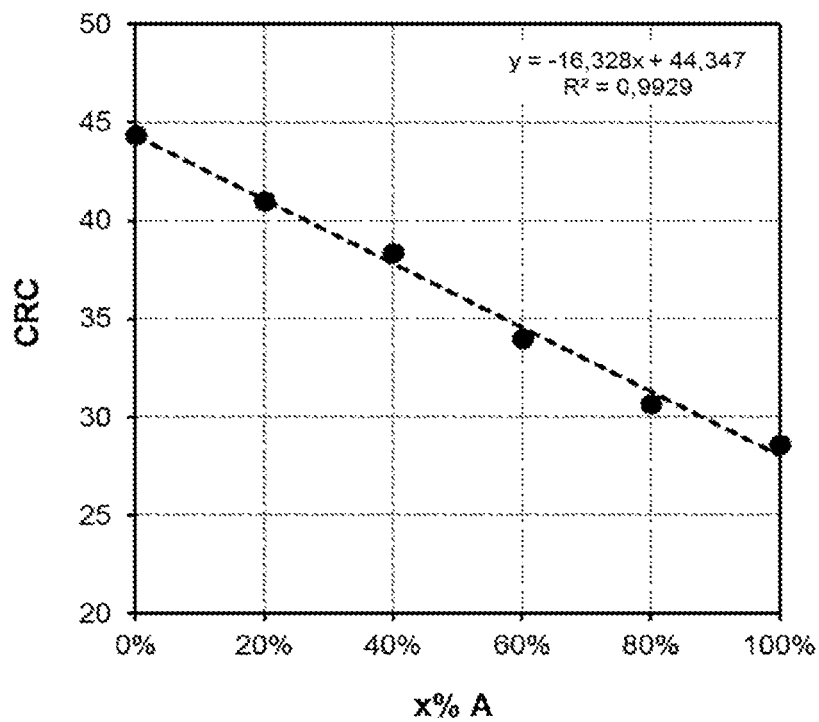

The results of table 4 are shown in FIGS. 7 and 8.

TABLE 5

Mixtures of superabsorbent A (example 3) and superabsorbent B (example 6)

| Example | Superabsorbent B | Superabsorbent A | CRC g/g | T20 s | VAUL s |
|---|---|---|---|---|---|
| 25*) | 100% | 0% | 34.0 | >1200 | 1398 |
| 26*) | 80% | 20% | 32.1 | 753 | 520 |
| 27*) | 60% | 40% | 29.9 | 222 | 177 |
| 28*) | 40% | 60% | 28.0 | 167 | 145 |
| 29 | 20% | 80% | 26.9 | 155 | 161 |
| 30*) | 0% | 100% | 26.0 | 165 | 180 |

*)comparative example

Figure 9:
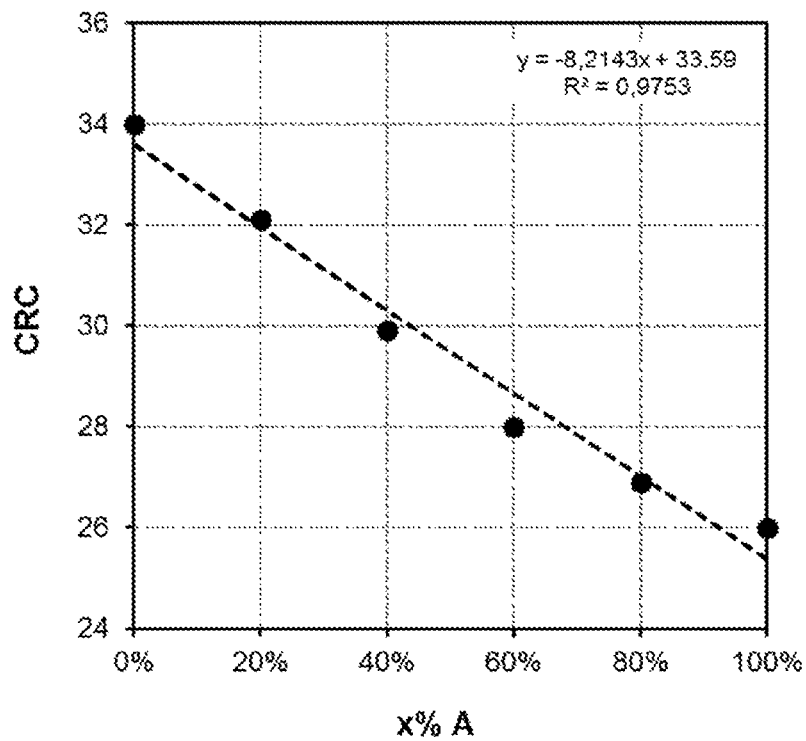
Figure 10:
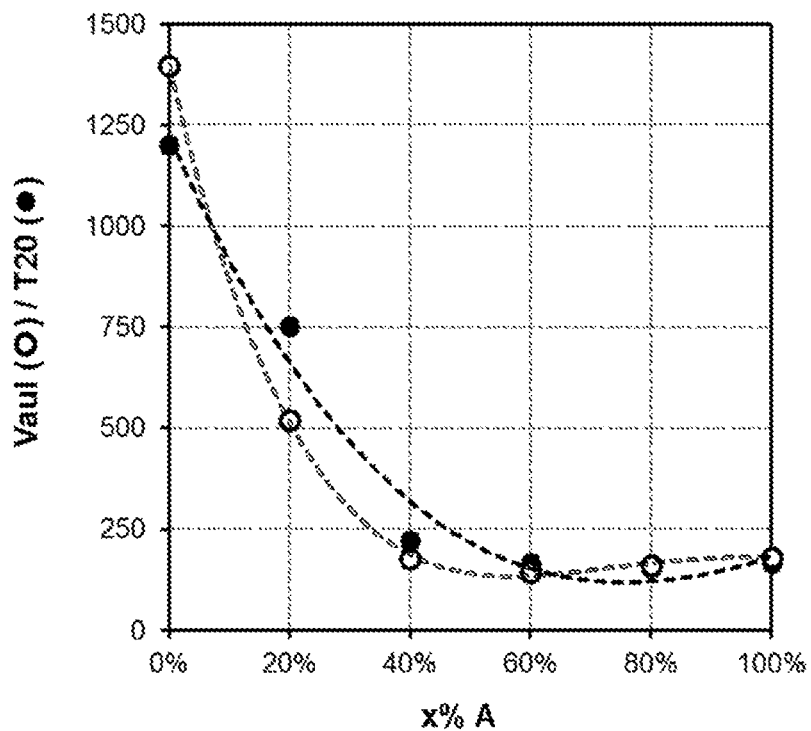

The results of table 5 are shown in FIGS. 9 and 10.

TABLE 6

Mixtures of superabsorbent A (example 3) and superabsorbent B (example 2)

| Example | Superabsorbent B | Superabsorbent A | CRC g/g | T20 s | VAUL s |
|---|---|---|---|---|---|
| 31*) | 100% | 0% | 33.4 | 285 | 362 |
| 32*) | 80% | 20% | 32.6 | 271 | 323 |
| 33*) | 60% | 40% | 29.3 | 217 | 287 |
| 34*) | 40% | 60% | 27.6 | 182 | 192 |
| 35 | 20% | 80% | 26.1 | 143 | 163 |
| 36*) | 0% | 100% | 26.0 | 165 | 180 |

*)comparative example

Figure 11:
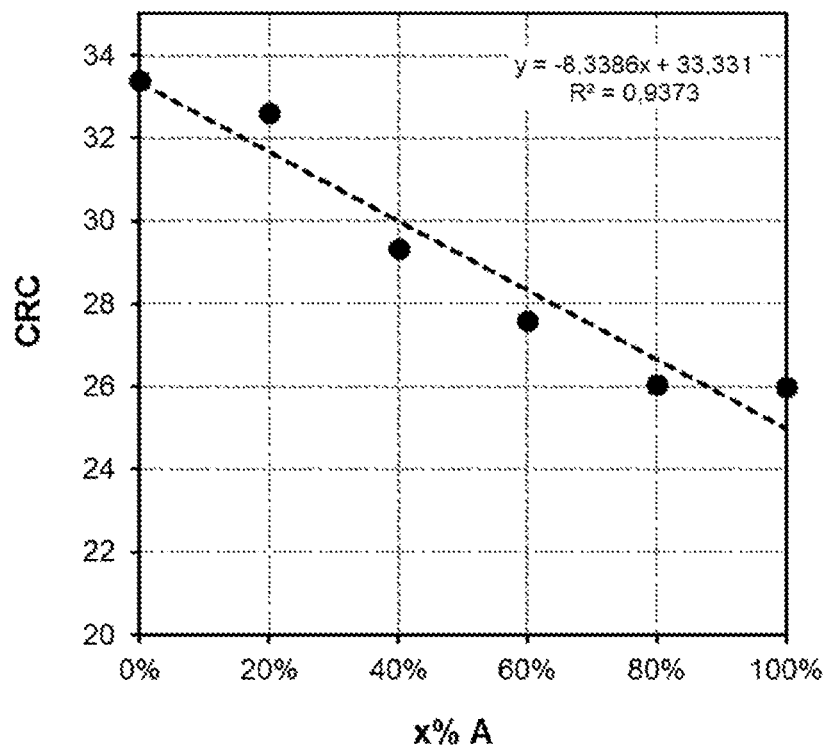
Figure 12:
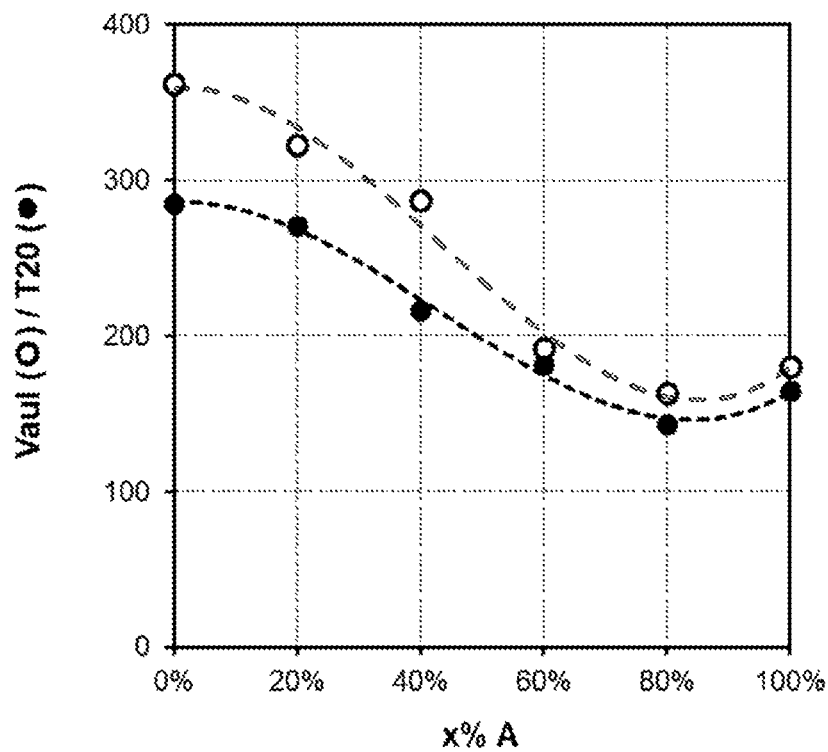

The results of table 6 are shown in FIGS. 11 and 12.

The invention claimed is:

1. A superabsorbent mixture M comprising at least 70% by weight of superabsorbent A having a liquid absorption of 20 g/g (T20) of less than 300 s and/or a volumetric liquid absorption under pressure 0.3 psi (2.07 kPa) (VAUL) with a τ value of less than 400 s, and at least 5% by weight of superabsorbent B having a centrifuge retention capacity (CRC) of at least 30 g/g.

2. The superabsorbent mixture M according to claim 1, wherein superabsorbent A has a liquid absorption of 20 g/g (T20) of less than 240 s and/or a volumetric liquid absorption under pressure 0.3 psi (2.07 kPa) (VAUL) with a τ value of less than 350 s.

3. The superabsorbent mixture M according to claim 1, wherein superabsorbent A has a liquid absorption of 20 g/g (T20) of less than 180 s and/or a volumetric liquid absorption under pressure 0.3 psi (2.07 kPa) (VAUL) with a τ value of less than 250 s.

4. The superabsorbent mixture M according to claim 1, wherein superabsorbent A has a liquid absorption of 20 g/g (T20) of less than 120 s and/or a volumetric liquid absorption under pressure 0.3 psi (2.07 kPa) (VAUL) with a τ value of less than 200 s.

5. The superabsorbent mixture M according to claim 1, wherein superabsorbent B has a centrifuge retention capacity (CRC) of at least 35 g/g.

6. The superabsorbent mixture M according to claim 1, wherein superabsorbent B has a centrifuge retention capacity (CRC) of at least 40 g/g.

7. The superabsorbent mixture M according to claim 1, wherein superabsorbent B has a centrifuge retention capacity (CRC) of at least 45 g/g.

8. The superabsorbent mixture M according to claim 1, wherein superabsorbent A has a mean sphericity (mSPHT) of less than 0.72.

9. The superabsorbent mixture M according to claim 1, wherein superabsorbent B has a mean sphericity (mSPHT) of greater than 0.72.

10. The superabsorbent mixture M according to claim 1, wherein superabsorbent A has a bulk density (ASG) of less than 0.70 g/ml.

11. The superabsorbent mixture M according to claim 1, wherein superabsorbent B has a bulk density (ASG) of greater than 0.70 g/ml.

12. The superabsorbent mixture M according to claim 1, wherein superabsorbent A has been surface postcrosslinked.

13. The superabsorbent mixture M according to claim 1, wherein superabsorbent B has not been surface postcrosslinked.

14. The superabsorbent mixture M according to claim 1, wherein superabsorbent A and/or superabsorbent B has an average particle size of 250 to 500 µm.

15. A hygiene article comprising a superabsorbent mixture M according to claim 1.

* * * * *